(12) United States Patent
Okada et al.

(10) Patent No.: US 6,933,374 B2
(45) Date of Patent: Aug. 23, 2005

(54) FARNESYL PYROPHOSPHATE SYNTHASE PROTEIN, NUCLEIC ACID AND PROMOTER REGION THEREOF

(75) Inventors: Yukio Okada, Gunma (JP); Kazutoshi Ito, Gunma (JP)

(73) Assignee: Sapporo Breweries Limited, Tokyo (JP)

( * ) Notice: Subject to any disclaimer, the term of this patent is extended or adjusted under 35 U.S.C. 154(b) by 1 day.

(21) Appl. No.: 10/148,188

(22) PCT Filed: Oct. 5, 2001

(86) PCT No.: PCT/JP01/08816

§ 371 (c)(1),
(2), (4) Date: Jul. 11, 2002

(87) PCT Pub. No.: WO02/31164

PCT Pub. Date: Apr. 18, 2002

(65) Prior Publication Data

US 2003/0148489 A1 Aug. 7, 2003

(30) Foreign Application Priority Data

Oct. 6, 2000 (JP) .................................... 2000-308054

(51) Int. Cl.[7] .......................... C12N 9/10; C12N 15/00; C12Q 1/48; C07H 21/04
(52) U.S. Cl. ...................... 536/23.2; 435/15; 435/320.1; 435/193; 536/24.1; 536/23.1
(58) Field of Search ...................... 435/193, 15, 320.1; 536/23.2, 23.1

(56) References Cited

FOREIGN PATENT DOCUMENTS

| EP | 0 955 363 | 11/1999 |
|---|---|---|
| EP | 1 033 405 | 9/2000 |
| EP | 1 063 297 | 12/2000 |
| WO | WO 95/00634 | 1/1995 |
| WO | WO 00/36081 | 6/2000 |
| WO | WO 01/44276 | 6/2001 |

OTHER PUBLICATIONS

Seffernick et al., J. Bacteriol. 183(8):2405–2410, 2001.*
Broun et al., Science 282:1315–1317, 1998.*
Arnold et al., GenEMBL accession No. AF268889, Jun. 2, 2001.*
Cunillera et al., GenEMBL accession No. L46367, Mar. 22, 2000.*
H–W. Heldt, Plant Biochemistry & Molecular Biology, pps. 360–376, "ISOPRENOIDS," 1997.
H. Tobe, et al., Biosci. Biotech. Biochem., vol. 61, No. 1, pps. 158–159, "Bone Resorption Inhibitors from Hop Extract," 1997 (with English translation).
P. R. Sanders, et al., Nucleic Acid Research, vol. 15, No. 4, pps. 1543–1558, "Comparison of Cauliflower Mosaic Virus 35S and Nopaline Synthase Promoters in Transgenic Plants," 1987.
J. Sambrook et al., Analysis and Cloning of Eukaryotic Genomic DNA, pps. 9.47 to 9.62 and 11.45 to 11.61, "Hybridization of Radiolabeled Probes to Immobilized Nucleic Acids," 1989.
D. B. Wagner, et al., Proc. Natl. Acad. Sci. USA, vol. 84, pps. 2097–2100, "Chloroplast DNA Polymorphisms in Lodgepople an Djack Pines and Their Hybrids," Apr. 1987.
Y–G. Liu, et al., Genomics, vol. 25, pps. 674–681, "Thermal Asymmetric Interlaced PCR: Automatable Amplification and Sequencing of Insert End Fragments from P1 and YAC Clones for Chromosome Walking," 1995.
Plant Molecular Biology Reporter, vol. 11, No. 2, pps. 113–116, "A Simple and Efficient Method for Isolating RNA from Pine Trees," 1993.
S. Attucci, et al., Archives of Biochemistry and Biophysics, vol. 321, No. 2, pps. 493–500, "Farnesyl Pyrophosphate Synthase from White Lupin: Molecular Cloning, Expression, and Purification of the Expressed Protein[1]," Aug. 20, 1995.
S. Attucci et al.: "Farnesyl pyrophosphate synthase from white lupin: molecular cloning, expression, and purification of the expressed protein" Arch. Biochem. Biophys., vol. 321, No. 2, pp. 493–500 1995.
Adiwilaga et al.: "Cloning and characterization of cDNA encoding farnesyl diphosphate synthase from rubber tree (*Heavea brasiliensis*)" Plant Mol. Biol., vol. 30, No. 5, pp. 935–946 1996.
Z. Pan et al.,: "Cloning, characterization, and heterologous expression of cDNAs for farnesyl diphosphate synthase from the guayule rubber plant reveals that this prenyltransferase occurs in rubber particles" Arch. Biochem. Biophys., vol. 332, No. 1, pp. 196–204 1996.
Y. Matsushita et al.: "Cloning and analysis of a cDNA encoding farnesyl diphosphate synthase from *Artemisia annua*." GENE., vol. 172, No. 2, pp. 207–209 1996.
Y. Okada, et al.: "Molecular clonging and expression of farnesyl pyrophosphate synthase gene responsible for essential oil biosynthesis in hop (*humulus*) *lupulus*" Journal of Plant Physiology, vol. 158, No. 9, pp. 1183–1188 2001.

(Continued)

*Primary Examiner*—Rebecca Prouty
*Assistant Examiner*—Delia M. Ramirez
(74) *Attorney, Agent, or Firm*—Oblon, Spivak, McClelland, Maier & Neustadt, P.C.

(57) ABSTRACT

The promoter region of the farnesyl pyrophosphate synthase gene that was expressed in the hop luplin gland in a specific manner was elucidated based on the genomic DNA of the hop farnesyl pyrophosphate synthase gene having the nucleotide sequence set forth in SEQ ID NO:2, the cDNA of the hop farnesyl pyrophosphate synthase gene having the nucleotide sequence set forth in SEQ ID NO:3, and the nucleotide sequence information on the genomic DNA and the cDNA. It will reveal the gene involved in the biosynthesis of secondary metabolites in a hop as well as the nucleotide sequence of the promoter gene that functions in the hop luplin gland in a tissue-specific manner. This will allow for the transformation of the hop by gene manipulations and the in vitro synthesis of the hop secondary metabolites.

5 Claims, 5 Drawing Sheets

OTHER PUBLICATIONS

Database NCBI, Jun. 2, 2001, Arnold C. M. et al., "Humulus Lupulus farnesyl pyrophosphate synthase mRNA, complete cds", Database accession no. AF268889 *Abstract*.

Database NCBI, Apr. 4, 2001, Okada Y. et al., "Cloning and analysis of farnesyl pyrophosphate synthase, complete cds", Database accession no. AB053487 *Abstract*.

Database NCBI, Aug. 25, 2001, Bamba T. et al., "Eucommia ulmoldes EUFPPSI mRNA for putative FPP synthase 1", 1, Database accession no. AB041626 *Abstract*.

Database NCBI, Jun. 28, 2001, Coulary–Salin B. et al., "Citrofortunella microcarpa farnesyldiphosphate synthase (FSP1)", Database accession no. AF390138 *Abstract*.

Database NCBI, Jun. 14, 2001, Asadaa T. et al., "Eucommia ulmoides EUFFPS2 mRNA for putative FPP synthase 2, complete cds", Database accesssion no. AB052681 *Abstract*.

Database NCBI, Jun. 19, 2001, Lange B. M. et al., Mentha piperita fameyl diphosphate synthase mRNA, complete cds, Database accession no. AF384040 *Abstract*.

Database NCBI, Apr. 25, 1999, Llaca V. et al., "Oryza sative subsp. Indica putative farnesyl pyrophosphate synthase", Database accession no. AF111710 *Abstract*.

Sabnuta Kazutsuka, et al, "Cloning of a cDNA that encodes farnesyl diphosphate synthase and the blue–light–induced expression of the corresponding gene in the leaves of rice plants"Biochimica et Biophysica Acta, vol. 1350, No. 3, 1997, pp. 240–246, issn: 0006–3002 *the whole document*.

Hugueney Philippe, et al., "Developmental and stress regulation of gene expression for plastid and cytosolic isoprenoid pathways in pepper fruits", Plant Physiology (Rockville), vol. 111, No. 2, 1996, pp. 619–626, ISSN: 0032–0889 *the whole document*.

Database NCBI, Nov. 13, 1998, Gaffe J. et al., "Lycopersicon esculentum farnesyl pyrphosphate synthase (FSP1)", Database accession no. AF048747 *Abstract*.

Chun P. L. et al., "Identification of a maize endosperm–specific cDNA encoding farnesyl pyrophosphate synthetase", Gene, Elsevier Biomedical Press, Amsterdam, NL, vol. 171, No. 2, Jun. 1, 1996, pp.193–196, ISSN: 0378–1119, * the whole document*.

Cunillera N. et al., "Arabidopsis thaliana contains two differentially expressed farnesyl–diphosphate synthase genes" Journal of Biological Chemistry, American Society of Biological Chemists, Baltimore, MD, U.S., vol. 271, No. 13, Mar. 29, 1996, pp. 7774–7780, ISSN: 0021–9258 *the whole document*.

Database NCBI, Nov. 21, 1998, Park S.C., et al., "Helianthus annuus farnesyl pyrophosphate synthase (FSP) mRNA", Database accession no. AF019892 * Abstract*.

Database NCBI, May 27, 1999, Chen D. et al., "Artemisia annua farnesyl diphosphate synthase (fsp2) mRNA, complete cds", Database accession no. AF136602 *Abstract*.

Chen Da–Hua, et al: "Expression of a chimeric farnesyl diphosphate synthase gene in Artemisia annua L. transgenic plants via Agrobacterium tumefaciens–mediated transformation", Plant Science (Shannon), vol. 155, No. 2, Jun. 29, 2000, pp. 179–185, issn: 0168–9452 *the whole document*.

* cited by examiner

SEQUENCE LISTING

<160> NUMBER OF SEQ ID NOS: 18

<210> SEQ ID NO 1
<211> LENGTH: 1029
<212> TYPE: DNA
<213> ORGANISM: Humulus lupulus L.
<220> FEATURE:
<221> NAME/KEY: CDS
<222> LOCATION: (1)..(1029)
<223> OTHER INFORMATION:

<400> SEQUENCE: 1

```
atg agt ggt tta agg tca aaa ttc atg gag gtt tac tcc att ttg aaa        48
Met Ser Gly Leu Arg Ser Lys Phe Met Glu Val Tyr Ser Ile Leu Lys
1               5                   10                  15 tca gag ctt ctc aac gat cct gct ttc gag ttc acc gat gat tct cgc        96
Ser Glu Leu Leu Asn Asp Pro Ala Phe Glu Phe Thr Asp Asp Ser Arg
                20                  25                  30 caa tgg gtc gaa cgg atg ctg gat tac aat gtc cca gga ggt aag ctt       144
Gln Trp Val Glu Arg Met Leu Asp Tyr Asn Val Pro Gly Gly Lys Leu
            35                  40                  45 aat cgt ggg ttg tca gtt att gat agt tac caa tta ctt aaa gga gga       192
Asn Arg Gly Leu Ser Val Ile Asp Ser Tyr Gln Leu Leu Lys Gly Gly
        50                  55                  60 aag gaa cta act gaa gaa gaa att ttt cta act tct gct ctt ggt tgg       240
Lys Glu Leu Thr Glu Glu Glu Ile Phe Leu Thr Ser Ala Leu Gly Trp
65                  70                  75                  80 tgt att gaa tgg ctt caa gca tat ttt ttg gtt ctt gat gat atc atg       288
Cys Ile Glu Trp Leu Gln Ala Tyr Phe Leu Val Leu Asp Asp Ile Met
                85                  90                  95 gat aac tct gtt aca cgt cgc ggt caa ccc tgc tgg ttt aga gta cca       336
Asp Asn Ser Val Thr Arg Arg Gly Gln Pro Cys Trp Phe Arg Val Pro
                100                 105                 110 aag gtt gga ttg att gct gca aac gat ggc att cta ctt cga aac cat       384
Lys Val Gly Leu Ile Ala Ala Asn Asp Gly Ile Leu Leu Arg Asn His
            115                 120                 125 att ccg aga att ctt aag aag cat ttc aag ggg aag agc tac tat gtg       432
Ile Pro Arg Ile Leu Lys Lys His Phe Lys Gly Lys Ser Tyr Tyr Val
        130                 135                 140 gat ctt ctt gat ttg ttt aat gag gtg gaa ttc caa aca gcc tcg gga       480
Asp Leu Leu Asp Leu Phe Asn Glu Val Glu Phe Gln Thr Ala Ser Gly
145                 150                 155                 160 caa atg att gat ttg atc acc aca att gaa gga gag aaa gat ctt tca       528
Gln Met Ile Asp Leu Ile Thr Thr Ile Glu Gly Glu Lys Asp Leu Ser
                165                 170                 175 aaa tac tca att cca ctt cac cat cgc att gtt cag tac aag act gct       576
Lys Tyr Ser Ile Pro Leu His His Arg Ile Val Gln Tyr Lys Thr Ala
            180                 185                 190 tac tac tca ttc tac ctt ccg gtt gct tgt gca ttg gtg atg gct ggt       624
Tyr Tyr Ser Phe Tyr Leu Pro Val Ala Cys Ala Leu Val Met Ala Gly
        195                 200                 205 gaa aat ctt gat aac cat gtt gat gtg aag aac gtc ctt att gaa atg       672
Glu Asn Leu Asp Asn His Val Asp Val Lys Asn Val Leu Ile Glu Met
    210                 215                 220 gga acc tat ttc caa gta cag gat gac tat ttg gat tgt ttt ggc cac       720
Gly Thr Tyr Phe Gln Val Gln Asp Asp Tyr Leu Asp Cys Phe Gly His
```

```
                                                              -continued 225                 230                 235                 240 cca gat gta att ggc aag att ggt aca gat att gaa gac ttc aag tgc     768
Pro Asp Val Ile Gly Lys Ile Gly Thr Asp Ile Glu Asp Phe Lys Cys
                245                 250                 255 tct tgg ttg gtt gtg aaa gca ctc gaa ata gct acc gag gaa caa aag     816
Ser Trp Leu Val Val Lys Ala Leu Glu Ile Ala Thr Glu Glu Gln Lys
            260                 265                 270 aag atg cta ttt gag cat tat ggt aag gga gat gaa gca tct gtc aaa     864
Lys Met Leu Phe Glu His Tyr Gly Lys Gly Asp Glu Ala Ser Val Lys
        275                 280                 285 aaa gtg aaa gag tta tac aag gcc ctt gat ctt gag ggc gtg ttt gcg     912
Lys Val Lys Glu Leu Tyr Lys Ala Leu Asp Leu Glu Gly Val Phe Ala
    290                 295                 300 gat tac gag aat gct agt tac caa aag ctt ata aaa tcg atc gaa gct     960
Asp Tyr Glu Asn Ala Ser Tyr Gln Lys Leu Ile Lys Ser Ile Glu Ala
305                 310                 315                 320 cat ccg aaa gaa gaa gtt cag gca gtg ctc aaa tct ttc ttg gct aag    1008
His Pro Lys Glu Glu Val Gln Ala Val Leu Lys Ser Phe Leu Ala Lys
                325                 330                 335 atc tac aag agg cag aag taa                                        1029
Ile Tyr Lys Arg Gln Lys
                340

<210> SEQ ID NO 2
<211> LENGTH: 342
<212> TYPE: PRT
<213> ORGANISM: Humulus lupulus L.

<400> SEQUENCE: 2

Met Ser Gly Leu Arg Ser Lys Phe Met Glu Val Tyr Ser Ile Leu Lys
1               5                   10                  15

Ser Glu Leu Leu Asn Asp Pro Ala Phe Glu Phe Thr Asp Asp Ser Arg
            20                  25                  30

Gln Trp Val Glu Arg Met Leu Asp Tyr Asn Val Pro Gly Gly Lys Leu
        35                  40                  45

Asn Arg Gly Leu Ser Val Ile Asp Ser Tyr Gln Leu Leu Lys Gly Gly
    50                  55                  60

Lys Glu Leu Thr Glu Glu Ile Phe Leu Thr Ser Ala Leu Gly Trp
65                  70                  75                  80

Cys Ile Glu Trp Leu Gln Ala Tyr Phe Leu Val Leu Asp Asp Ile Met
            85                  90                  95

Asp Asn Ser Val Thr Arg Arg Gly Gln Pro Cys Trp Phe Arg Val Pro
        100                 105                 110

Lys Val Gly Leu Ile Ala Ala Asn Asp Gly Ile Leu Leu Arg Asn His
    115                 120                 125

Ile Pro Arg Ile Leu Lys Lys His Phe Lys Gly Lys Ser Tyr Tyr Val
130                 135                 140

Asp Leu Leu Asp Leu Phe Asn Glu Val Glu Phe Gln Thr Ala Ser Gly
145                 150                 155                 160

Gln Met Ile Asp Leu Ile Thr Thr Ile Glu Gly Glu Lys Asp Leu Ser
            165                 170                 175

Lys Tyr Ser Ile Pro Leu His His Arg Ile Val Gln Tyr Lys Thr Ala
        180                 185                 190

Tyr Tyr Ser Phe Tyr Leu Pro Val Ala Cys Ala Leu Val Met Ala Gly
    195                 200                 205

Glu Asn Leu Asp Asn His Val Asp Val Lys Asn Val Leu Ile Glu Met
210                 215                 220
```

```
Gly Thr Tyr Phe Gln Val Gln Asp Asp Tyr Leu Asp Cys Phe Gly His
225                 230                 235                 240

Pro Asp Val Ile Gly Lys Ile Gly Thr Asp Ile Glu Asp Phe Lys Cys
            245                 250                 255

Ser Trp Leu Val Val Lys Ala Leu Glu Ile Ala Thr Glu Glu Gln Lys
            260                 265                 270

Lys Met Leu Phe Glu His Tyr Gly Lys Gly Asp Glu Ala Ser Val Lys
        275                 280                 285

Lys Val Lys Glu Leu Tyr Lys Ala Leu Asp Leu Glu Gly Val Phe Ala
    290                 295                 300

Asp Tyr Glu Asn Ala Ser Tyr Gln Lys Leu Ile Lys Ser Ile Glu Ala
305                 310                 315                 320

His Pro Lys Glu Glu Val Gln Ala Val Leu Lys Ser Phe Leu Ala Lys
                325                 330                 335

Ile Tyr Lys Arg Gln Lys
            340

<210> SEQ ID NO 3
<211> LENGTH: 4699
<212> TYPE: DNA
<213> ORGANISM: Humulus lupulus L.

<400> SEQUENCE: 3
```

| | | | | | |
|---|---|---|---|---|---|
| tgagaaggat | tttggcagcc | tcttaaattt | gacaaaattt | tgattggtta | tatatatata | 60 |
| tatgtttaca | tttattgtgt | atgcttgcca | acaacatat | gatgatatat | tactttttg | 120 |
| tcctcactct | ttgattttgt | tttttattat | tctaaacttt | gtaattttcc | attcaagctt | 180 |
| acatttctat | catatattat | aatattattt | ttgtcatatt | aattatatca | aaatacaaaa | 240 |
| aattaacatt | ttagtctatt | ttacaaaatc | tactaaaatt | aatttccatt | ttgatattaa | 300 |
| aaaaataaaa | cattcatata | aaattgacca | aaagctaatg | tatggttaat | tttgataaat | 360 |
| aatgtaaaac | attatataat | tactaagttt | tcttaaatta | acataaagtc | taatatttag | 420 |
| ctaaaatcaa | ataatatatt | tcttatataa | aagcaataaa | aaaagtggt | cttgtatgat | 480 |
| tattcaattt | tttttctttg | tttaattttt | ctatgtcata | catattataa | caataataag | 540 |
| attcttttac | ataacatgaa | ttttttccat | ttgagtttag | atgagtctac | tttgctcttt | 600 |
| aaaggaaaaa | ttataacaat | aacatgagtt | tttttttttt | catttaagtt | tttttgctc | 660 |
| cttaatagta | aatattagtt | aatatatata | attttaaaaa | aatatttttt | tttaaattaa | 720 |
| tctattcaac | cactaaattt | cattttagta | gtcaatctca | tacaaataca | aacattataa | 780 |
| ttacacataa | atcattactc | taataatata | taataaaata | aagaagagtt | tttttcttaa | 840 |
| ttaaaattat | tttgttttca | cacattataa | caataaataa | tgagaggttc | ttacatatga | 900 |
| aactcattta | atttaacaat | atttgtctat | catgctcttt | aaataaaaaa | taacaacaat | 960 |
| aacaattatt | atattatata | tatattatat | aggacaattc | tctttatacc | ctaccgaata | 1020 |
| gtttacagta | ccaaaaatta | ggttaaaaaa | tattgttttc | tacgcacata | aaaaaaaaat | 1080 |
| taatcacggg | tgtaacaaca | tgtttgaatt | tagttttcgt | tactgtaaac | tattcagaat | 1140 |
| tttatgaaaa | tttgcagatg | ctctaaataa | ctacaatata | tacggtcata | aaaaaaatcg | 1200 |
| cgccgaaaac | tgttcacaag | tcaagaacac | tgagagtctc | atcggtaaag | cttaaattgt | 1260 |
| agccctataa | aagaattatc | ctataaatat | atattgtatt | tatacatttt | tagactctgt | 1320 |
| gttttgacaa | attatttttt | ggaccctata | ttttgtaaaa | tagttcaaat | aagcccttaa | 1380 |

```
tcctgatttt gatgaacaaa aaattaagta taacaagaca gttcttatgt agaatgatta    1440 tattttttgtt ctgagttgtt agtttgatga attatttgtt atttttgttc aaaaaacttt    1500
gatcaaaatc gagtttaggg gtctatttga actattttag aaaacacaag gtctaaaaaa    1560
taatttatca aaacacaggt ccaaacaagt aatgagacaa atacagaat  tttaaaaaat    1620 ataaacccat atatatatat atatttaaaa aatggcaaat tgtaattat  atgataaatg    1680 aagccctaat gttgatgatt taaacaatgc atgattggtc aaaacaagtg gcctccaaag    1740
ctctataaag agagcacttc tacactgact ctctctctct atctgtctct atatatatat    1800
atttatatat agattttcag tatcacagac cagaacaagt acaacccatt agtcccacct    1860
ctgttgagct cttgttcagc caaaaatga  gtggtttaag gtcaaaattc atggaggttt    1920
actccatttt gaaatcagag cttctcaacg atcctgcttt cgagttcacc gatgattctc    1980
gccaatgggt cgaacgggta ttcccatctc tctaactctc ttctttttc  actgacattg    2040 cttttcgtttt ctccatttta tggaatttgg gttctgattt tgtagttct  caccagattc    2100 gttttggtct tttcaattca aactattttt ttatatgtaa aagtggaaac tagaacatat    2160
ttccttaaaa gatctggact tttagctgaa aattttggtg ggttataatt attttctta    2220 aattagttat attatgctca gattttatct gatcttgttc attgaagaat cctcttcacc    2280
atgtttaaat actgtgttat tattatcgta ttctctcttt agttttttca ttaagattct    2340
ctattgtact gacttgtacc ttattaaaaa aacctgattg agtgtcatta tacttatttt    2400
ctttcaatta ctgagactat gctcagattt tatatgatct tgttcattga agagtcatgc    2460
ttagaccaag ttcaatttct ctgtgtagtt ctttctttaa gattctttat tgtacttagt    2520
tgagccttat aaaaagacct gattgagtgt catttttac  tttgcagatg ctggattaca    2580
atgtcccagg aggtttggaa tgcaactctt ttttcacttc ctttgacctg tttgtgttga    2640
gaatgattgt aatgaactgt gacattttac cttctttaac aaattcatat tgatttttc    2700 tggttggtag gtaagcttaa tcgtgggttg tcagttattg atagttacca attacttaaa    2760
ggaggaaagg aactaactga agaagaaatt tttctaactt ctgctcttgg ttggtgtatt    2820
gaatgggtat gcagctttca ttttggtact ttttattcat taattgggat acccttttaa    2880
cactttgtaa cattcaattc tatgtagctt caagcatatt ttttggttct tgatgatatc    2940
atggataact ctgttacacg tcgcggtcaa ccctgctggt ttagagtacc aaaggtgtga    3000
ctttacatcc tttcatgggg ttttttctctt gttttctatg gagtgaatat cctaacatgt    3060
gtaagtgttc tgcgtttatc acaggttgga ttgattgctg caaacgatgg cattctactt    3120
cgaaaccata ttccgagaat tcttaagaag catttcaagg ggaagagcta ctatgtggat    3180
cttcttgatt tgtttaatga ggtgtgattt gtttgatgga tagttgagta gagcaaaagg    3240
gtttcttttt ctttgtcatc ttagtcatgt aacagggttt gttaatctac aggtggaatt    3300
ccaaacagcc tcgggacaaa tgattgattt gatcaccaca attgaaggag agaaagatct    3360
ttcaaaatac tcaattccac tgtaagtgaa attgatatgt gtgattacta caagactttc    3420
actcaaatat tcgatgtgcc taagattgt  ggtgttgtct tgcagtcacc atcgcattgt    3480
tcagtacaag actgcttact actcattcta ccttccggta agagagaacc gttgatttat    3540
gcattcatga agcatgttgc cttgattggt tttcatcttt gtctttgata gttctgcttg    3600
ttttgataat cttttctcatg taagaatcta tcaactgcgc ttatgtatcg ttctctgaca    3660
ctaattatga tcaggttgct tgtgcattgg tgatggctgg tgaaaatctt gataaccatg    3720
ttgatgtgaa gaacgttctt attgaaatgg gaacctattt ccaagtacag gtgattgcag    3780
```

```
acatatcctc atttgtatat tcttgagaaa tatagttgca aatgtattga ccaaatcttt    3840
tggccactga tcctgataat cttgctgaac attttactgt attttttattg acaaaaaaac    3900 caatgacata ttatgtagga tgactatttg gattgttttg gccacccaga tgtaattggc    3960
aaggtatgtt ataaagccac actcttttgt caagtttgta atgcactatc ctcattcaac    4020
tgggaatttt tttcagtttt cattgatgcc cttttggatt atcagattgg tacagatatt    4080
gaagacttca agtgctcttg gttggttgtg aaagcactcg aaatagctac cgaggaacaa    4140
aagaagatgc tatttgtaag caataaagtt catcctttca attttttacat gaaaatgtct    4200 cgagggaacg ttggttactt ttgcttacac atctgaattc tgtgttttcc aggagcatta    4260
tggtaaggga gatgaagcat ctgtcaaaaa agtgaaagag ttatacaagg cccttgatct    4320
tgaggttcat tctctctgtt tctctttcga tctatgtttt taaagctcgt ggagtaaccc    4380
tcttctaact tcgattttttg ggatttgtag ggcgtgtttg cggattacga gaatgctagt    4440
taccaaaagc ttataaaatc gatcgaagct catccgaaag aagaagttca ggcagtgctc    4500
aaatctttct tggctaagat ctacaagagg cagaagtaag gttgaaaatg gagatttgga    4560
ctaaagagat aacaatcaac tttgtgtggg cattagcatt tctttcactc tttttaataa    4620
aagggtcatt tttagtgatt gttttttggtt aatcataaga attcttagtt catcttatgc    4680
tgagtggtgg atattttaa                                                 4699
```

<210> SEQ ID NO 4  
<211> LENGTH: 18  
<212> TYPE: DNA  
<213> ORGANISM: ARTIFICIAL SEQUENCE  
<220> FEATURE:  
<223> OTHER INFORMATION: SYNTHETIC DNA

<400> SEQUENCE: 4

```
ggytggtgya ttgaatgg                                                    18
```

<210> SEQ ID NO 5  
<211> LENGTH: 23  
<212> TYPE: DNA  
<213> ORGANISM: ARTIFICIAL SEQUENCE  
<220> FEATURE:  
<223> OTHER INFORMATION: SYNTHETIC DNA

<400> SEQUENCE: 5

```
taaaaygart artargchgt ytt                                              23
```

<210> SEQ ID NO 6  
<211> LENGTH: 25  
<212> TYPE: DNA  
<213> ORGANISM: ARTIFICIAL SEQUENCE  
<220> FEATURE:  
<223> OTHER INFORMATION: SYNTHETIC DNA

<400> SEQUENCE: 6

```
cctttggtac tctaaaccag caggg                                            25
```

<210> SEQ ID NO 7  
<211> LENGTH: 25  
<212> TYPE: DNA  
<213> ORGANISM: ARTIFICIAL SEQUENCE  
<220> FEATURE:  
<223> OTHER INFORMATION: SYNTHETIC DNA

<400> SEQUENCE: 7

-continued

```
ttacaaagtg ttaaagggt atccc                                          25

<210> SEQ ID NO 8
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
aggtggaatt ccaaacagcc tcggg                                         25

<210> SEQ ID NO 9
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
tttgatcacc acaattgaag gagag                                         25

<210> SEQ ID NO 10
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
gacattgtaa tccagcatct gc                                            22

<210> SEQ ID NO 11
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
cacagagaaa ttgaacttgg tc                                            22

<210> SEQ ID NO 12
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
cacttccttt gacctgtttg                                               20

<210> SEQ ID NO 13
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
aagctcgtgg agtaaccctc                                               20

<210> SEQ ID NO 14
<211> LENGTH: 20
<212> TYPE: DNA
<213> ORGANISM: ARTIFICIAL SEQUENCE
```

```
<220> FEATURE:
<223> OTHER INFORMATION: SYNTHETIC DNA

<400> SEQUENCE: 14
gcgtgtttgc ggattacgag                                              20

<210> SEQ ID NO 15
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
tgagaaggat tttggcagcc                                              20

<210> SEQ ID NO 16
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
gaattcttat gattaaccaa aaac                                         24

<210> SEQ ID NO 17
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 17
cgggatccat gagtggttta aggtcaaaat                                   30

<210> SEQ ID NO 18
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
cgggatcctt acttctgcct cttgtagatc                                   30
```

US 6,933,374 B2

FARNESYL PYROPHOSPHATE SYNTHASE PROTEIN, NUCLEIC ACID AND PROMOTER REGION THEREOF

TECHNICAL FIELD

This invention relates to farnesyl pyrophosphate (FPP) synthase genes of hop and their promoter regions.

BACKGROUND ART

Plants produce and accumulate within their bodies, numerous kinds of low molecular weight organic compounds such as terpenoids, alkaloids, phenolics, and saponins. It was initially thought that these compounds were not directly responsible for the life maintenance of organisms and have only auguxilliary functions; therefore, they were referred to as "secondary metabolites."

However, in recent years it has been beginning to be understood that these secondary metabolites function as substances responsible for the cell differentiation or the defense against exogenous factors. Concurrently, the methods of utilization are being found in the broad fields of taste products, drugs and pigments. Not to mention the agricultural field, their utility is catching attention in broad fields.

Because such secondary metabolites are valuable in being industrially utilized, the elucidation of their formation process in plant cells has progressed and presently it has been shown that the substances are synthesized through a complex cascade involving a large number of enzymes. Direct Extraction from plants is, however, needed to obtain such substances. In those cases the quantities that can be isolated at one time are very small, resulting in high cost. Therefore, it has been desired that in vitro synthetic methods using gene manipulations or cultured cells be developed.

Farnesyl pyrophosphate synthase is known as an enzyme that is involved in the synthetic cascade of the secondary metabolites in plants. Farnesyl pyrophosphate synthase is an enzyme that is involved in the metabolism of isoprenoids which forms the basis for a variety of substances in plants such as pigments, odorants, phytohormones, phytoalexins, and defense substances against pests (Plant Biochemistry & Molecular Biology, Hans-Walter Heldt, Oxford University Press, pp. 360–376, 1997). It has been shown that farnesyl pyrophosphate synthase catalyzes the reaction converting isopentenyl pyrophosphate into geranyl pyrophosphate by adding dimethylallyl pyrophosphate thereto as well as catalyzes the reaction converting said geranyl pyrophosphate into farnesyl pyrophosphate by adding isopentenyl pyrophosphate thereto.

Hop is a principal material to give beer refreshing bitter taste and flavor. It is beginning to be understood that the secondary metabolites are secreted in large quantities in luplin gland contained in the cone of the hop and these secondary metabolites greatly contribute to the bitter taste and flavor of beer. Further, in recent years it has been shown that the secondary metabolites of the hop possess pharmacological actions (for example, Biosci. Biotech. Biochem., 61 (1), 158, 1997). Under such circumstances, a variety of breeding improvements are being made to the hop with an emphasis on the secondary metabolites accumulated in the luplin gland such as bitter substances and essential oil constituents.

However, the hop is a dioecious plant. Especially, the male plant does not beer cones that serves as the beer material and thus is not regarded important commercially. Very little study, therefore, has been carried out and the genetic traits that will be useful for fermentation have been hardly elucidated. For these reasons, conventional breeding methods through crossing largely rely on experience and intuition. The present situation is that the brewing qualities are totally unpredictable until the cones have grown. Accordingly, it is strongly desired that the farnesyl pyrophosphate synthase gene be isolated from a hop and that the control of the secondary metabolites in the hop and in vitro synthetic methods be established according to an approach using gene manipulations.

The breeding methods utilizing genetic engineering such as transformation techniques and molecular selection techniques are becoming possibilities in various plants. In these methods, more objective and efficient breeding is possible as compared to the conventional breeding methods which largely rely on experience and intuition. More specifically, the transformation technique is one in which an exogenous gene is introduced into a plant cell to have it expressed and the trait to be desirably incorporated is directly introduced into the cell. In order to have the exogenous gene expressed, the following method may be employed: an objective structural gene and a terminator operable in a plant cell are linked to an operable promoter capable of regulating the expression of the gene in the plant cell and the linkage is introduced into the plant cell. For a promoter that is frequently used at the experimental level, there are mentioned, among others, a CaMV 35S promoter, a nopaline synthase gene promoter both of which can express transgenes in relatively large kinds of plants regardless of their tissues (Sanders P. R. et al., Nucleic Acid Res, 15 (1987) 1543–1558). However, when the aforementioned promoters are used to express the transgenes in all the tissues, some transgenes may do harm to the growth of the plants. It is, therefore, strongly desired that tissue-specific promoters capable of expressing exogenous genes in the objective tissue be isolated.

DISCLOSURE OF THE INVENTION

This invention has been made in view of the problems that are inherent in the aforementioned prior art; it aims at elucidating the genes involved in the biosynthesis of secondary metabolites in a hop and the nucleotide sequences (base sequences) of the promoters operable in a tissue-specific manner in the luplin gland of the hop as well as aims at allowing for the transformation of the hop by gene manipulations and the in vitro synthesis of the secondary metabolite of the hop.

As a result of having pursued diligent investigations to accomplish the above-stated objects, the present inventors found farnesyl pyrophosphate synthase genes and their promoter genes, which led to the completion of this invention: the farnesyl pyrophosphate synthase genes were strongly expressed in the luplin gland of the hop and were involved in the biosynthesis of secondary metabolites.

Specifically, according to this invention there are provided the proteins described in 1–2 below:

1. A protein having the amino acid sequence set forth in SEQ ID NO:1 in the Sequence Listing.
2. A protein having an amino acid sequence derivable from the deletion or the substitution of one or more amino acids in the amino acid sequence set forth in SEQ ID NO:1 in the Sequence Listing, or from the addition of one or more amino acids to the amino acid sequence set forth in SEQ ID NO:1 in the Sequence Listing, said protein possessing the farnesyl pyrophosphate synthase activity.

Also, according to this invention there are provided the nucleic acids described in 3–10 below:

3. A nucleic acid encoding a protein having the amino acid sequence set forth in SEQ ID NO:1 in the Sequence Listing.

4. A nucleic acid having the nucleotide sequence set forth in SEQ ID NO:3 in the Sequence Listing.

5. A nucleic acid comprising a part of the nucleotide sequence set forth in SEQ ID NO:3 in the Sequence Listing.

6. A nucleic acid that hybridizes to a nucleic acid having the nucleotide sequence set forth in SEQ ID NO:3 in the Sequence Listing or to a complementary nucleic acid thereof under stringent conditions, said nucleic acid encoding a protein possessing the farnesyl pyrophosphate synthase activity.

7. A nucleic acid having the nucleotide sequence set forth in SEQ ID NO:2 in the Sequence Listing.

8. A nucleic acid comprising a part of the nucleotide sequence set forth in SEQ ID NO:2 in the Sequence Listing.

9. A nucleic acid having a nucleotide sequence of from base No. 1 to base No. 1886 in the nucleotide sequence set forth in SEQ ID NO:2 in the Sequence Listing.

10. A nucleic acid that hybridizes to a nucleic acid having the nucleotide sequence described in 7 or 8 above or to a complementary nucleic acid thereof under stringent conditions, said nucleic acid possessing promoter activity.

The use of these proteins or nucleic acids will then enable the transformation of a hop by gene manipulations as well as enable the in vitro synthesis of the secondary metabolites of a hop.

BEST MODE FOR CARRYING OUT THE INVENTION

Figure 1:
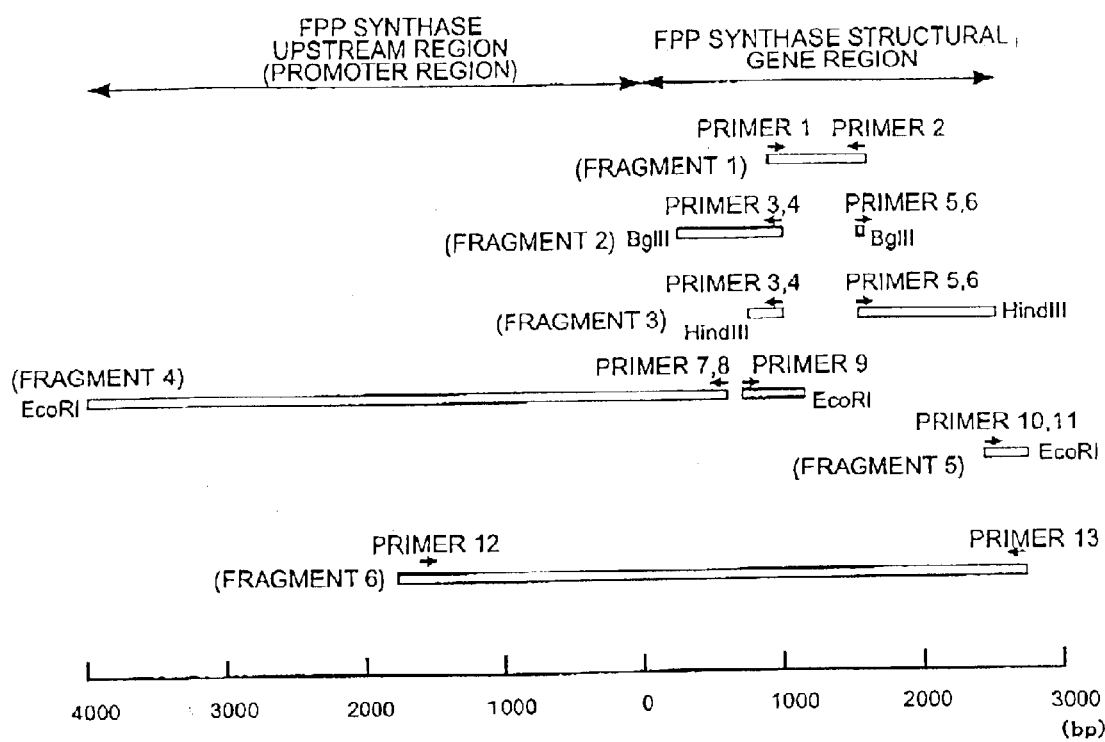
FIG. 1 is a diagram showing nucleic acid fragments obtained from the isolation process of a farnesyl pyrophosphate synthase gene of this invention.

The preferred embodiments of this invention will be described in detail hereafter by referring to the drawings when necessary.

As used in the invention, "nucleic acid" refers to DNA, RNA, or a polynucleotide that may be a derivatized active DNA or RNA among others. Preferred are DNA and/or RNA. In this case, the forms of the nucleic acid include genomic DNA, cDNA and mRNA, for example.

As used in the invention, "hybridize under stringent conditions" means that two nucleic acid fragments hybridize to each other under the hybridization conditions as described in Sambrook, J. et al., "Expression of Cloned Genes in *E. coli*," Molecular Cloning: A Laboratory Manual (1989) Cold Spring Harbor Laboratory Press, New York, USA, 9.47–9.62 and 11.45–11.61.

More specifically, "stringent conditions" means that after hybridization in 6.0×SSC at about 45° C., washing is to be done in 2.0×SSC at 50° C., for example. For the purpose of selection of stringency, the salt concentration in the washing step can be selected to be from about 2.0×SSC at 50° C. under low stringency to about 0.1×SSC at 50° C. under high stringency. Furthermore, the temperature of washing step can be increased from room temperature under low stringency conditions (about 22° C.) to about 65° C. under high stringency conditions.

As used in the invention, "promoter" refers to a nucleotide sequence present in DNA that is a signaling sequence functioning to govern directing the initiation and termination of RNA synthesis (transcription) or directing the regulation of its frequency.

As used in the invention, "promoter activity" refers to the function of initiating, terminating, and regulating transcription by the promoter as described above.

The hop farnesyl pyrophosphate synthase of this invention will be first described.

The protein of this invention is a hop farnesyl pyrophosphate synthase protein having the amino acid sequence with 342 amino acid residues, as set forth in SEQ ID NO:1 in the Sequence Listing.

Also, the protein of the invention may be a protein having an amino acid sequence derivable from the deletion or the substitution of one or more amino acids in the amino acid sequence set forth in SEQ ID NO:1 in the Sequence Listing, or from the addition of one or more amino acids to the amino acid sequence set forth in SEQ ID NO:1 in the Sequence Listing, insofar as it possesses the farnesyl pyrophosphate synthase activity.

Further, since sugar chains may be appended to a large number of proteins, the addition of sugar chains can be adjusted by subjecting one or more amino acids to conversion. Therefore, proteins for which the addition of sugar chains within the amino acid sequence set forth in SEQ ID NO:1 in the Sequence Listing has been adjusted are also embraced by the proteins of this invention insofar as they possess the farnesyl pyrophosphate synthase activity as described above.

Further, nucleic acids having nucleotide sequences encoding the aforementioned farnesyl pyrophosphate synthase proteins are also embraced by the invention. Specifically, because a plurality of nucleotide sequences (or codons) encoding a single amino acid exist, there are a large number of nucleic acids encoding the amino acid sequence set forth in SEQ ID NO:1 in the Sequence Listing. These nucleic acids are thus embraced by the nucleic acids of this invention. As used herein, "encode a protein" means that when DNA is double-stranded, the term includes a DNA wherein either of the complementary two strands is provided with the nucleotide sequence encoding the protein. Therefore, embraced by the invention are nucleic acids comprising the nucleotide sequences directly encoding the amino acid sequence set forth in SEQ ID NO:1 in the Sequence Listing and nucleic acids comprising the nucleotide sequences complementary to the foregoing nucleotide sequences.

Next, the farnesyl pyrophosphate synthase genes according to the invention will be described.

The nucleic acid of this invention is one (cDNA) having the nucleotide sequence set forth in SEQ ID NO:3 in the Sequence Listing and encoding a hop farnesyl pyrophosphate synthase.

The nucleic acid of the invention may also be a part of the nucleotide sequence set forth in SEQ ID NO:3 in the Sequence Listing.

Further, the nucleic acid of the invention may be one that hybridizes to the nucleotide sequence with 1029 bases set forth in SEQ ID NO:3 in the Sequence Listing under stringent conditions and encoding a protein possessing the farnesyl pyrophosphate synthase activity; and its nucleotide sequence is not particularly limited insofar as it satisfies these conditions. Still further, the nucleic acids of the invention embrace nucleic acids having nucleotide sequences complementary to that of the aforementioned nucleic acid undergoing hybridization under stringent conditions. Specifically, there are mentioned, among others, nucleic acids having deletions of, substitutions of, insertions to or additions to several bases of the nucleic acid having the nucleotide sequence of SEQ ID NO:3 and possessing the farnesyl pyrophosphate synthase activity. As used herein, "deletion, substitution, insertion, or addition" includes not only a short deletion, substitution, insertion or addition with 1 to 10 bases, but also a long deletion, substitution, insertion or addition with 10 to 100 bases. The "farnesyl pyrophosphate synthase activity" refers to the activity allowing the reaction to proceed by which farnesyl pyrophosphate is synthesized by the catalytic action of the farnesyl pyrophosphate synthase. In this case the substance that serves as a substrate for the farnesyl pyrophosphate synthase is not particularly limited insofar as it is a substance from which farnesyl pyrophosphate can be ultimately synthesized. Specifically, there are mentioned isopentenyl pyrophosphate and geranyl pyrophosphate.

The geranyl pyrophosphate and farnesyl pyrophosphate are regarded in a hop as the precursors of essential oil constituents such as myrcenes, humulenes, caryophyllenes, and farnesenes. Thus, by detecting a nucleic acid having the nucleotide sequence set forth in SEQ ID NO:3 in the Sequence Listing, it will be possible to utilize the nucleic acid as a genetic marker for the traits concerning the regulation of the metabolic system for hop's essential oil constituents and the essential oil constituents themselves. The detection of a nucleic acid does not require the whole nucleotide sequence set forth in SEQ ID NO:3 in the Sequence Listing; for example, part of the sequence may be amplified by PCR and the detection may be carried out by gene analysis techniques such as nucleotide sequencing (base sequencing) or RFLP (Restriction Fragment Length Polymorphism). Therefore, the nucleic acids of this invention embrace nucleic acids comprising a part of the nucleotide sequence set forth in SEQ ID NO:3 in the Sequence Listing.

Next, the promoter region of the farnesyl pyrophosphate synthase gene according to this invention will be described.

The nucleic acid of this invention is a nucleic acid having the nucleotide sequence set forth in SEQ ID NO:2 in the Sequence Listing. The nucleic acid of the invention may be part of the nucleic acid having the nucleotide sequence with 4699 bases, as set forth in SEQ ID NO:2 in the Sequence Listing, or alternatively it may be the nucleotide sequence represented by base no. 1 to no. 1886.

The nucleic acid having the nucleotide sequence set forth in SEQ ID NO:2 is genomic DNA of farnesyl pyrophosphate synthase and the nucleotide sequence encoding the starting methionine of farnesyl pyrophosphate synthase is from base no. 1887 to no. 1889 within the genomic DNA. Thus, base no. 1 to no. 1886 in the nucleotide sequence set forth in SEQ ID NO:2 in the Sequence Listing is a 5'-noncoding region, within which the promoter region of the farnesyl pyrophosphate synthase gene is contained. It will be difficult to unambiguously define the boundaries of both ends of the promoter region within base no. 1 to no. 1886; therefore, the nucleic acids of this invention embrace sequences comprising part of base no. 1 to no. 1886 insofar as they possess the promoter activity.

The nucleic acid of this invention may be one that hybridizes to the nucleic acid having the nucleotide sequence set forth in SEQ ID NO:2 or to the nucleic acid having the nucleotide sequence represented by base no. 1 to no. 1886 within the foregoing nucleic acid under stringent conditions and that possess the promoter activity; and its nucleotide sequence is not particularly limited. The nucleic acids of this invention further embrace nucleic acids having the nucleotide sequence complementary to that of the nucleic acid that undergoes hybridization under stringent conditions and that possesses the promoter activity. Specifically, there are mentioned, among others, nucleic acids having one or more deletions in, substitutions in, insertions to or addition to the nucleic acid having the nucleotide sequence of SEQ ID NO:2 and possessing the promoter activity. As used herein, "deletion, substitution, insertion, or addition" includes not only a short deletion, substitution, insertion or addition with 1 to 10 bases, but also a long deletion, substitution, insertion or addition with 10 to 100 bases.

Next, the preferred method of isolating the nucleic acids of this invention and analyzing the functions of their gene products will be described.

The nucleic acid of the invention can be isolated through steps (1) to (5) as described below and it is possible to confirm in steps (6) to (7) that the isolated gene will display the farnesyl pyrophosphate synthase activity or will possess the promoter activity.

1. Isolation of Farnesyl Pyrophosphate Synthase Gene and its Promoter from a Hop (1) Preparation of Hop Genomic DNA The preparation of the hop genomic DNA can be carried out according to a method known in the art: for example, the method of Wagner, D. B. et al. (Proc. Natl. Acad. Sci. USA 84, 2097–2100 (1987)) can be followed.

(2) Isolation of Farnesyl Pyrophosphate Synthase Gene and its promoter

Figure 2:
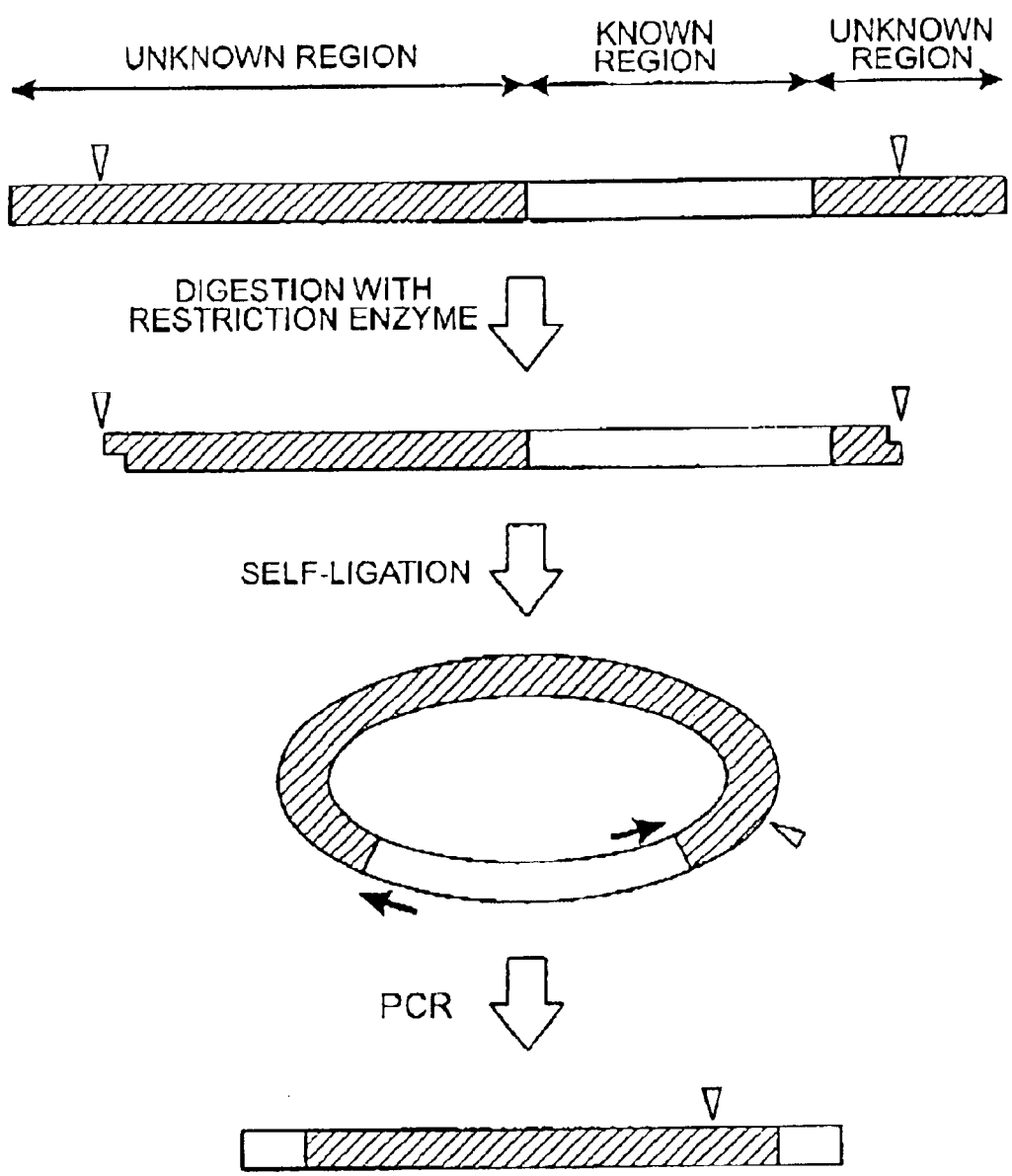
FIG. 2 is a schematic diagram showing the principle of Inverse PCR used in the invention.
Figure 3:
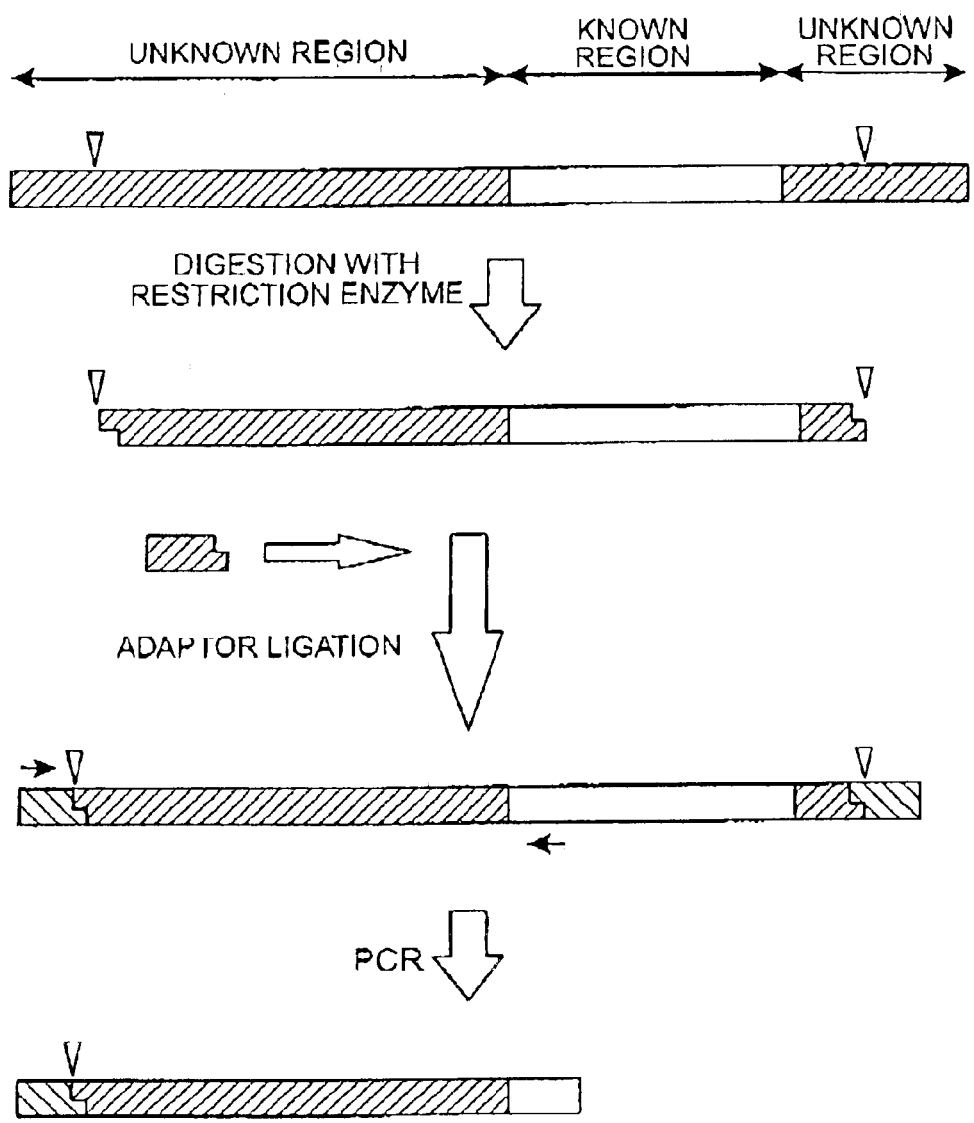
FIG. 3 is a schematic diagram showing the principle of Casette-ligation mediate PCR used in the invention.

Partial fragments of the farnesyl pyrophosphate synthase gene can be isolated by designing primers based on the known nucleotide sequences of the farnesyl pyrophosphate synthase genes from other plants such as Arabidopsis and corn and by using the known methods such as Inverse PCR or Cassette-ligation mediated PCR. As Inverse PCR is shown in the schematic diagram of FIG. 2, DNA that serves as a sample is digested with restriction enzymes; the restriction enzyme-digested product is then cyclized to a sample that serves as a template prior to amplification; and primers synthesized in directions opposite to those for the primers to be used in ordinary PCR are used to perform PCR. The method makes it possible to amplify the upstream or downstream region adjacent to a specific nucleotide sequence. As a concrete example of Inverse PCR, there may be mentioned the method of Liu, Y. G. et al. (Genomics 25, 674–681 (1995)). As schematically shown in FIG. 3, Cassette-ligation Mediated PCR is a method to be used when an unknown nucleotide sequence adjacent to a known nucleotide sequence will be desirably determined (e.g., the method as described in the protocol attached to a Takara LA PCR in vitro Cloning Kit (Takara Shuzo Co. Ltd.)). Specifically, the nucleic acid containing such nucleic acid region is first digested with restriction enzyme. Adapter nucleic acids of known nucleotide sequences having the restriction enzyme recognition sites from which primers can be designed are ligated to the aforementioned nucleic acid. Then, the unknown nucleotide sequence region flanked by the known sequence regions is amplified by PCR and the amplified product may be sequenced. By repeating such Inverse PCR and/or Cassette-ligation Mediated PCR, it is possible to isolate the entire region of the hop farnesyl pyrophosphate synthase gene and its promoter.

(3) Sequencing

The isolated genes can be sequenced by a method known in the art: for example, it can be done by following the protocol attached to an ABI PRISM Dye Primer Cycle Sequencing Ready Reaction Kit available from PE Biosystems Inc. The nucleotide sequences determined by the aforementioned method can be subjected to homology search using a database such as http://www.ncbi.nlm.nih.gov/BLAST and thus it will be possible to find out the presence or absence of homology with the known genes obtained from other species of plants as well as the degree of homology. This will enable determination as to whether or not the obtained genes are novel.

(4) Preparation of Total RNA from the Respective Tissue Fractions

After an arbitrary fraction has been prepared, the preparation of total RNA can be carried out according to a method known in the art: for example, the method of Chang, S. et al. (Plant Molecular Biology Report 11, 113–116 (1993)) can be followed.

(5) Isolation of Farnesyl Pyrophosphate Synthase Gene cDNA cDNA of the farnesyl pyrophosphate synthase gene can be isolated according to a method known in the art: specifically, primers may be designed based on the nucleotide sequence of the genomic DNA for the farnesyl pyrophosphate synthase gene isolated in (2) and cDNA synthesized from the total mRNA may be used as a template to effect isolation through RT-PCR. For a concrete method in this case, the method as described in the protocol attached to a Titan One Tube RT-PCR System available from Roche Diagnostics Inc. can be employed, for example.

(6) Functional Analysis of the Protein Encoded by the Isolated Farnesyl Pyrophosphate Synthase Gene The protein encoded by the farnesyl pyrophosphate synthase gene isolated in (5) can be expressed in $E.$ $coli$ cells by incorporating cDNA of the farnesyl pyrophosphate synthase gene into an expression vector and introducing the vector into an $E.$ $coli$ cell. The expression and purification of the protein encoded by the farnesyl pyrophosphate synthase gene described above can, for example, be carried out by the method as described in the protocol attached to a QIAexpress Expression System (QIAGEN Inc.). The functions of the farnesyl pyrophosphate synthase protein expressed in those $E.$ $coli$ cells and purified can be confirmed by a method known in the art: for example, the method of Sylvie A. et al. (Arch. Biochem. Biophys. 321, 493–500, (1995)) can be used for confirmation.

(7) Northern Hybridization (Hereunder Referred to as "Northern Analysis")

The isolated farnesyl pyrophosphate synthase gene can be used as a probe and Northern analysis can be done to analyze as to in which tissue the isolated farnesyl pyrophosphate synthase gene is expressed, or as to in which tissue the isolated farnesyl pyrophosphate synthase functions. For example, the analysis can be done by the method as described in "The DIG System User's Guide for Filter Hybridization" (Boeringer Manheim) p. 53–55 (1995).

Next, one embodiment that is made possible by the nucleic acid of this invention will be described.

(1) Probes for Use in Hybridization

By using a part or the whole of the nucleotide sequence disclosed in this invention as a hybridization probe, it is possible to at least detect the farnesyl pyrophosphate synthase gene expressed in a hop. By using a part or the whole of the nucleotide sequence disclosed in this invention as a hybridization probe to investigate the gene expression in hop tissues, it is also possible to identify the distribution of the gene expression.

When a part or the whole of the nucleotide sequence disclosed in this invention is used as a hybridization probe, the method of hybridization itself is not particularly limited; however, there are specifically mentioned as examples, Northern hybridization, Southern hybridization, colony hybridization, dot hybridization, Fluorescence in situ hybridization (FISH), in situ hybridization (ISH), DNA chip method, and microarray method.

When the nucleotide sequence of this invention is used as the hybridization probe, the nucleotide length (base length) of at least 20 bases is necessary; and a gene having a nucleotide length of 20 or more consecutive bases within the gene sequence of the invention is preferably used. There are used more preferably, one having a nucleotide length of 40 or more bases, and most preferably one having a nucleotide length of 60 or more bases.

The nucleic acid probe technique is well known to one skilled in the art, and suitable hybridization conditions for the probes with individual lengths according to this invention and the objective polynucleotide can readily be determined. To obtain hybridization conditions optimal for the probes containing varying lengths, such manipulations are well known to one skilled in the art. For example, Sambrooks et al., "Molecular Cloning: A Laboratory Manual," 2nd. Ed., Cold Spring Harbor (1989) may be referred to.

Here, the probes are preferably labeled so that they can be easily detected. Detectable labels may be any type or a portion thereof that can be detected either by the naked eyes or with a device. The detectable labels that are ordinarily used are, for example, radioactive labels such as $^{32}P$, $^{14}C$, $^{125}I$, $^{3}H$, and $^{35}S$. Biotin-labeled nucleotides can be incorporated into nucleic acids by using nick translation, chemical and enzymatic means, or the like. The biotin-labeled probes are detected after hybridization utilizing labeling means such as avidin/streptavidin, fluorescent labels, enzymes, and gold colloidal complexes. The nucleic acids may be labeled by being bound to proteins. Alternatively, there may be used nucleic acids that have cross-linked to the radioactive or fluorescent histone single strand biding protein.

(2) Primers for Use in PCR

It is also possible to detect the farnesyl pyrophosphate synthase gene by using as primer any sequence of the disclosed nucleotide sequence and the Polymerase Chain Reaction (PCR) method. For example, RNA can be extracted from a sample to be assayed and the gene expression can be semi-quantitatively determined by RT-PCR. Such a method can be carried out by a technique well known in the art.

When the nucleic acid of this invention is used as a PCR primer, the nucleotide length of from 10 to 60 bases is necessary; and a nucleic acid having a nucleotide length of from 10 to 60 consecutive bases (more preferably 15 to 30 bases) within the nucleic acid of the invention is preferably used. Generally, the GC content of the primer sequence is preferably from 40 to 60%. Further, it is preferred that there be no difference in Tm value between two primers. It is also preferred that annealing do not take place at the 3'-ends of the primers and a secondary structure do not occupy within the primers.

(3) Screening for Nucleic Acids

It is possible to detect the distribution of expression of the farnesyl pyrophosphate synthase gene that is expressed in a hop by using a part or the whole of the nucleotide sequence disclosed in this invention. For example, the part or the whole of the nucleotide sequence disclosed in the invention can be used as a hybridization probe or as a primer in PCR to detect the distribution of gene expression.

DNA chips, microarrays or the like can also be used to detect said distribution of gene expression. Specifically, parts or the whole of the nucleotide sequence disclosed in this invention can all be applied onto the chip or the array directly. RNA extracted from cells is labeled with a fluorescent substance or the like and is hybridized to the chip or the array; it is then possible to analyze as to in which cell the gene is highly expressed. DNA applied onto the chip or the array may be a PCR product obtained by using the part or the whole of the nucleotide sequence disclosed in this invention.

(4) DNA Cloning

It is possible to clone a gene that is expressed at least in a hop by using a part or the whole of the nucleotide sequence disclosed in this invention. For example, the part or the whole of the nucleotide sequence disclosed in the invention can be used as a probe in Northern hybridization or in colony hybridization, or as a primer in PCR to clone the part or the whole of the nucleotide sequence disclosed in this invention.

In embodiments other than those described above, it will be possible to obtain information on the hop farnesyl pyrophosphate synthase or to carry out the transformation of a hop and the production of its secondary metabolic products.

Specifically, the farnesyl pyrophosphate synthase mentioned above is an enzyme involved in the metabolism of isoprenoids on which a variety of substances in plants (such as pigments, odorants, phytohormones, phytoalexins and defense substances against pests) are based. Therefore, by using the farnesyl pyrophosphate synthase genes isolated as mentioned above, it will be possible to control the plant metabolic systems for pigments, odorants, phytohormones, phytoalexins, and defense substances against pests and to detect the genes responsible for these traits.

It will also be possible to produce the secondary metabolites of plants in vitro by using the farnesyl pyrophosphate synthase produced through gene manipulations using the farnesyl pyrophosphate synthase genes isolated in this invention.

There appears to be the possibility that farnesyl pyrophosphate synthase is involved in the metabolic systems of a hop for hop resin (hop resin constituents) and xanthohumol (Brauwelt, 36, 1998) the latter of which is said to possess anticancer action. It will further be possible to control the metabolic systems for the hop resin and xanthohumol by using the nucleic acids of this invention as well as to utilize said nucleic acids as genetic makers for the hop resin and xanthohumol.

Accordingly, it will be possible to carry out the method of breeding a hop through gene manipulations that conventionally have had to rely on experience and intuition. For example, a plant transformation technique is utilized to introduce the farnesyl pyrophosphate synthase gene of this invention into a hop. It will thus be possible to control the composition of the secondary metabolites in luplin gland. Accordingly, it will become possible to improve and maintain the qualities of foods utilizing hops (e.g., beer and low malt beer) as well as to improve and maintain the qualities of drugs utilizing the secondary metabolites.

BY utilizing the nucleic acid containing the promoter region of the farnesyl pyrophosphate synthase gene according to this invention, a gene to be desirably introduced into an objective hop and a terminator capable of functioning in the hop are linked to the downstream of the promoter, and this is introduced to the hop. The aforementioned gene will thus be allowed to be specifically expressed in the luplin gland.

EXAMPLES

This invention will be described more concretely by referring to the examples; however, the invention is not to be limited by these examples.

Example 1

Preparation of Hop Genomic DNA

The preparation of hop genomic DNA was carried out in the following manner described. Specifically, the leaves of a hop was freeze-ground in liquid nitrogen, suspended in a 2% CTAB solution [2% cetyltrimethylammonium bromide, 0.1 M Tris (pH 9.5), 20 mM EDTA, 1.4 M NaCl, 5% β-mercaptoethanol], and incubated at 65° C. for 30 minutes. After the suspension was extracted with chloroform/isoamyl alcohol (24:1) twice, DNA and RNA was allowed to precipitate by adding a ¾-fold amount of isopropanol. The precipitated DNA and RNA was dissolved in a High Salt TE buffer [1M sodium chloride, 10 mM Tris (pH 8.0), 1 mM EDTA] and it was incubated with addition of RNase at 60° C. to decompose only RNA. To this was added a two-fold amount of isopropanol, resulting in the precipitation of DNA. The precipitated DNA was washed with 70% ethanol and was then dissolved to prepare a genomic DNA sample.

Example 2

Isolation of Farnesyl Pyrophosphate Synthase Gene and its Promoter

Out of the amino acid sequences of farnesyl pyrophosphate synthase for *Arabidopsis*, corn, guayule, *Hevea*, white lupin, and pepper whose nucleotide sequences were known, the sequence that was consensus among the respective plants was made a basis on which Primer 1 (SEQ ID NO:4) and Primer 2 (SEQ ID NO:5) were synthesized. These primers were used together with the hop genomic DNA as a template to carry out PCR, producing Fragment 1 in FIG. 1.

Next, the resulting amplified fragment was sequenced. Primer 3 (SEQ ID NO:6), Primer 4 (SEQ ID NO:7), Primer 5 (SEQ ID NO:8), and Primer 6 (SEQ ID NO:9) shown in Table 1 were designed based on the obtained nucleotide sequence, and Inverse PCR was performed to obtain Fragments 2 and 3 in FIG. 1.

TABLE 1

| Primer | SEQ ID No. | Nucleotide sequence |
|---|---|---|
| 1 | 4 | 5'-GGYTGGTGYATTGAATGG-3' |
| 2 | 5 | 5'-TAAAAYGARTARTARGCHGTYTT-3' |
| 3 | 6 | 5'-CCTTTGGTACTCTAAACCAGCAGGG-3' |
| 4 | 7 | 5'-TTACAAAGTGTTAAAAGGGTATCCC-3' |
| 5 | 8 | 5'-AGGTGGAATTCCAAACAGCCTCGGG-3' |
| 6 | 9 | 5'-TTTGATCACCACAATTGAAGGAGAG-3' |
| 7 | 10 | 5'-GACATTGTAATCCAGCATCTGC-3' |
| 8 | 11 | 5'-CACAGAGAAATTGAACTTGGTC-3' |

TABLE 1-continued

| Primer | SEQ ID No. | Nucleotide sequence |
|---|---|---|
| 9 | 12 | 5'-CACTTCCTTTGACCTGTTTG-3' |
| 10 | 13 | 5'-AAGCTCGTGGAGTAACCCTC-3' |
| 11 | 14 | 5'-GCGTGTTTGCGGATTACGAG-3' |
| 12 | 15 | 5'-TGAGAAGGATTTTGGCAGCC-3' |
| 13 | 16 | 5'-GAATTCTTATGATTAACCAAAAAC-3' |
| 14 | 17 | 5'-CGGGATCCATGAGTGGTTTAAGGTTCAAAAT-3' |
| 15 | 18 | 5'-CGGGATCCTTACTTCTGCCTCTTGTAGATC-3' |

Specifically, the hop genomic DNA was digested with restriction enzymes BglII or HindIII. A DNA Ligation Kit Ver. 1 (Takara Shuzo Co. Ltd.) was used to carry out self-ligation following the protocol attached thereto. After the self-ligation was completed, a portion of the reaction solution was used as a template to carry out PCR by employing Primers 3 and 5. Subsequently, a portion of the reaction solution for which the PCR had been completed was used as a template to carry out PCR by employing Primers 4 and 6 shown in Table 1. Fragments 2 and 3 in FIG. 1 were thus obtained.

Similarly, Primer 7 (SEQ ID NO:10), Primer 8 (SEQ ID NO:11), and Primer 9 (SEQ ID NO:12) were designed based on the nucleotide sequence of Fragment 2 in FIG. 1. The hop genomic DNA digested with restriction enzyme EcoRI was subjected to self-ligation, and this was used as a template to carry out PCR again by employing Primers 7 and 9 described above. Fragment 4 in FIG. 1 was thus obtained and it was sequenced.

Fragment 5 in FIG. 1 was isolated with a Takara LA PCR in vitro Cloning Kit (Takara Shuzo Co. Ltd.) by Casette-ligation mediated PCR according to a protocol attached thereto. Specifically, the hop genomic DNA was digested with restriction enzyme EcoRI and to this was linked an EcoRI adapter included in the kit. PCR was next carried out by using Primer 10 (SEQ ID NO:13) that had been designed on the basis of the nucleotide sequence of Fragment 3 and cassette primer C1 included in the kit. This PCR reaction solution was further used as a template to carry out PCR by employing Primer 11 (SEQ ID NO:14) that had been designed on the basis of the nucleotide sequence of Fragment 3 and cassette primer C2 included in the kit. Fragment 5 was thus obtained and it was sequenced.

Finally, PCR was carried out by using the hop genomic DNA as a template and Primer 12 (SEQ ID NO: 15) and Primer 13 (SEQ ID NO: 16) that had been designed on the basis of Fragment 4 and Fragment 5 in FIG. 1, respectively. Fragment 6 was thus obtained that contained the hop farnesyl pyrophosphate synthase gene and a promoter thereof. All the PCR manipulations described above were carried out using an Expand High-Fidelity PCR System (Boeringer Manheim AG) according to the protocol attached thereto.

Example 3
Sequencing of the Hop Farnesyl Pyrophosphate Synthase Gene and its Promoter Both ends of Fragment 6 containing the hop farnesyl pyrophosphate synthase gene and its promoter that had been obtained in Example 2 were made blunt by using a Takara BKL Kit (Takara Shuzo Co. Ltd.) and it was subcloned into a pUC vector. The protocol attached to the kit was followed to make both ends of Fragment 6 blunt and to effect the subcloning into the pUC vector.

Sequencing was carried out using an ABI PRISM Dye Terminator Cycle Sequencing Ready Reaction Kit (ABI373S type available from PE Biosystem Inc.) according to the protocol attached thereto. The nucleotide sequence of Fragment 6 is shown in SEQ ID NO:2 in the Sequence Listing.

Example 4
Preparation of the Respective Tissue Fractions and Total RNA

The leaves, stem, luplin (−), and luplin (+) fractions of a hop were prepared for the tissues from which total RNA would be extracted. As used herein, "luplin (−) fraction" was a fraction principally recovered from the bract of a cone where luplin gland was hardly present. The "luplin (+) fraction" was a fraction consisting principally of luplin gland that was obtained by removing from the cone, tissues other than the luplin gland as much as possible. These tissue fractions were freeze-ground in liquid nitrogen, suspended in a 2% CTAB solution [2% cetyltrimethylammonium bromide, 0.1 M Tris (pH 9.5), 20 mM EDTA, 1.4 M NaCl, 5% β-mercaptoethanol], and incubated at 65° C. for 10 minutes. After the suspension was extracted with chloroform/isoamyl alcohol (24:1) twice, a ⅓-fold amount of 10M lithium chloride was added to the extract and it was allowed to stand overnight. After centrifugation at 15,000 rpm for 10 minutes, the precipitates are dissolved in water. When total RNA was to be used in Example 5, the precipitates were dissolved in DNase reaction buffer [100 mM sodium acetate (pH 5.2), 5 mM magnesium chloride] in place of water and it was incubated with addition of DNase at 37° C. to decompose only DNA. To the solution was further added a ⅓-fold amount of 10 M lithium chloride. It was allowed to stand overnight and centrifuged at 15,000 rpm for 10 minutes. After washing, the precipitates were washed with 70% ethanol and were then dissolved in water again to prepare a total RNA sample.

Example 5
Isolation and Sequencing of cDNA for the Farnesyl Pyrophosphate Synthase Gene Both ends of the coding region for the hop farnesyl pyrophosphate synthase gene were presumed that was set forth in SEQ ID NO:2 and sequenced in Example 3 based on the information about the farnesyl pyrophosphate synthase gene of *Arabidopsis* (among others) or the like the nucleotide sequence of which was known. Primers were designed that had the sequences obtained by appending the BamHI recognition sequence to those sequences and they were used with the total RNA produced in Example 4 as a template, where cDNA of the farnesyl pyrophosphate synthase gene was isolated by RT-PCR. Specifically, Primer 14 (SEQ ID NO:17) and Primer 15 (SEQ ID NO:18) were used as primers and PCR was carried out using a Titan One Tube RT-PCR System (Roche Diagnostics Inc.) according to the protocol attached thereto. The thus obtained cDNA of the farnesyl pyrophosphate synthase gene was subcloned into a PCR2.1 vector (Invitrogen Inc.) to prepare pFPPS101R. The subcloned cDNA of the farnesyl pyrophosphate synthase gene was sequenced using an ABI PRISM Dye terminator Cycle Sequencing Ready Reaction Kit (PE Biosystems Inc.) and a DNA sequencer ABI 373S type (PE Biosystems Inc.) according to the protocol attached thereto. The nucleotide sequence of cDNA for the obtained farnesyl pyrophosphate synthase gene is shown in SEQ ID NO:3 in the Sequence Listing. The amino acid sequence of the protein encoded by this cDNA is shown in SEQ ID NO:1.

Within the nucleotide sequence set forth in SEQ ID NO:3, the 660th base differed from the corresponding base (the 3737th base in SEQ ID NO:2) in the genomic DNA, although confirmation of the nucleotide sequences was conducted plural times. This is thought to be a base incorporation error resulting from RT-PCR conducted when cDNA was isolated. However, this error does not affect the functional analysis of protein as will be described in Example 6 because it leads to the amino acid identical to that which should have been encoded at the amino acid level.

Example 6
Functional Analysis of the Protein Encoded by the Isolated Farnesyl Pyrophosphate Synthase Gene In order to determine whether or not the protein encoded by the isolated farnesyl pyrophosphate synthase gene possessed the farnesyl pyrophosphate synthase activity, cDNA of the farnesyl pyrophosphate synthase gene isolated in Example 5 was treated with restriction enzyme BamHI to give DNA. The DNA was incorporated into the BamHI site of an expression vector pQE30 [attached to a QIAexpress Expression System (QIAGEN Inc.)]. It was then introduced into $E.\ coli$ to have the farnesyl pyrophosphate synthase gene expressed in the $E.\ coli$ cells and the expressed product was purified. Expression of the farnesyl pyrophosphate synthase gene in the $E.\ coli$ cells and purification of the expressed product was carried out according to the protocol attached to a QIAexpress Expression System (QIAGEN Inc.).

Next, the method of Sylvie A. et al. (Arch. Biochem. Biophys. 321, 493–500 (1995)) was followed to determine whether or not the obtained expression product possessed the farnesyl pyrophosphate synthase activity. Specifically, to 100 $\mu$l of enzyme reaction solution (50 mM Tris-HCl, 2 mM dithioerythritol, 1 mM magnesium chloride, 100 $\mu$M dimethylallyl pyrophosphate) were added 2 $\mu$l (28 $\mu$g) of the purified expression product of the farnesyl pyrophosphate synthase gene and 2.5 $\mu$l (0.05 $\mu$Ci) of $^{14}$C-isopentenyl pyrophosphate, and the reaction was allowed to take place at 30° C. for 30 minutes. To alkaline phosphatase (Wako Pure Chemical Industries, Ltd.) was added 30 $\mu$l of 10-fold concentration reaction buffer (as attached). Alkaline phosphatase, 1 $\mu$l, (10 units) was then added to the reaction, which was allowed to continue at 37° C. for 3 hours. Then, the reaction was further continued at 25° C. overnight. To the reaction solution was added 1 $\mu$l of farnesol (4.5 nmol) as a carrier and further 200 $\mu$l of hexane, and upon mixing the hexane layer was recovered after centrifugation at 10,000 rpm for one minute. Hexane, 100 $\mu$l, was again added to the remaining water layer and it was mixed and centrifuged to recover a hexane layer, which was combined with the hexane layer recovered earlier. The hexane extract was concentrated to 1 $\mu$l by being blown with nitrogen gas. After 10 $\mu$l of methanol was added and mixed to the concentrate, 1 $\mu$l was spotted onto thin layer chromatography (HPTLC-aluminum sheets silica gel 60 F254 pre-coated available from Merk KGaA) and developed in a developing solvent (benzene:ethyl acetate=9:1). Farnesol and geraniol were simultaneously spotted as a standard. After the thin layer chromatogram plate for which development had been completed was dried, iodine was sprayed onto the plate to ascertain the positions of farnesol and geraniol. Exposure to a X-ray film was carried out at −80° C. for 7 days. The obtained results are shown in FIG. 4.

Figure 4:
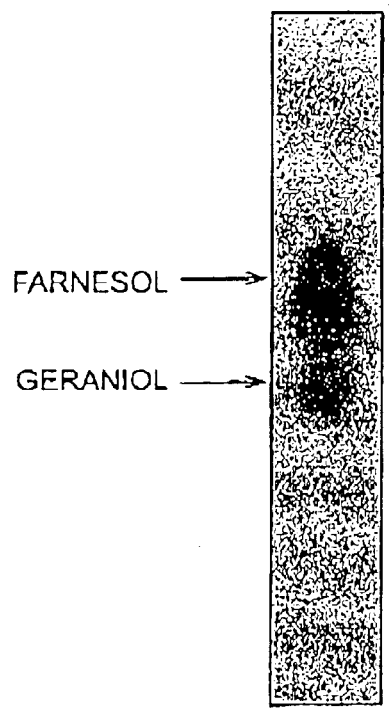
FIG. 4 is a representation showing the developed image of thin layer chromatography used when the activity of the farnesyl pyrophosphate synthase of the invention was determined.

As FIG. 4 shows, the signals of the reaction products were detected at the positions of farnesol and geraniol. Specifically, it was confirmed that the protein encoded by the isolated farnesyl pyrophosphate synthase gene possessed the farnesyl pyrophosphate synthase activity.

Example 7
Northern Hybridization

Northern hybridization was carried out to determine in which tissue of a hop the isolated farnesyl pyrophosphate synthase gene was expressed as well as to determine the level of its expression.

Plasmid pFPPS101R prepared in Example 5 was first digested with restriction enzyme KpnI to produce a linearized form. A DIG RNA labeling kit (SP6/T7) (Roche Diagnostics Inc.) was used to prepare a RNA probe for the farnesyl pyrophosphate synthase gene by employing the linearized form as a template. The preparation method was performed according to the protocol attached to the kit.

The total RNAs for the leaves, the stem, the luplin (−) fraction, and the luplin (+) fraction that had been prepared in Example 4 (each 15 $\mu$l) were subjected to electrophoresis using denatured agarose gel (1.2% agarose, 6.7% formaldehyde, 20 mM MOPS, 5 mM sodium acetate, 1 mM EDTA, pH 7.0). The gel for which electrophoresis had been completed was shaken in distilled water three times each for 40 minutes and after formaldehyde in the agarose gel was removed, RNA in the agarose gel was transferred to a nylon membrane by using 20×SSC (0.3 M sodium citrate, 3 M sodium chloride, pH 7.0) as buffer. The nylon membrane to which RNA had been transferred and the aforementioned probe were used to carry out hybridization at 68° C. overnight. Here, the composition of the hybridization buffer used in the hybridization was 5×SSC, 0.02% SDS, 0.1% N-lauroylsarcosin, 50% formamide, and 2% Blocking Reagent (Roche Diagnostics Inc.). After hybridization, a detergent (0.1% SDS, 2×SSC) was used to carry out washing-treatment twice each at 68° C. for 30 minutes; further, a detergent (0.1% SDS, 0.1×SSC) was used to carry out washing-treatment twice each at 68° C. for 30 minutes. After washing, the RNA fragment to which the probe had been hybridized was detected. The detection was carried out according to the protocol described in "The DIG System User's Guide for Filter Hybridization" (Roche Diagnostic Inc.). The results obtained are shown in FIG. 5.

Figure 5:
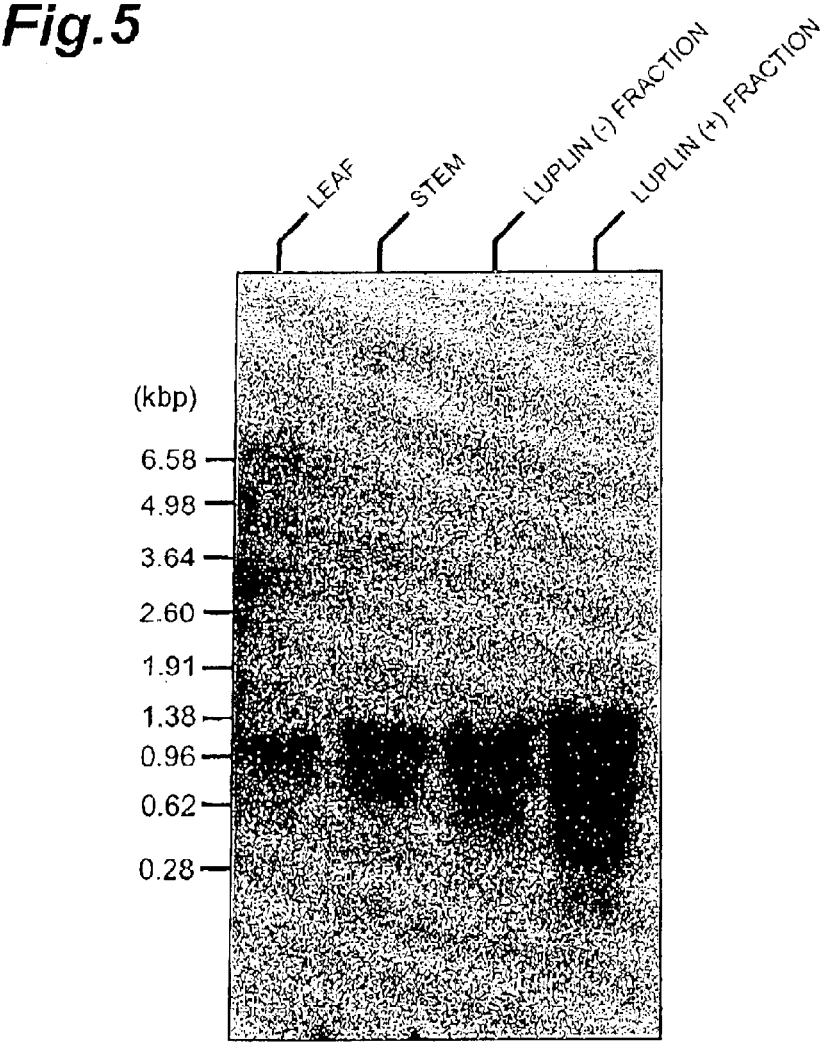
FIG. 5 is a photograph of Northern analysis that confirmed the expression of the farnesyl pyrophosphate synthase gene of the invention.

From the results of FIG. 5, there was observed in each of the tissue fractions, the leave, the stem, the luplin (−) fraction, and the luplin (+) fractions a signal at the position of 1.1 kb approximating to the size of the nucleic acid having the nucleotide sequence set forth in SEQ ID NO:2 in the Sequence Listing that encodes the farnesyl pyrophosphate synthase gene. This confirmed that the hop farnesyl pyrophosphate synthase gene was expressed in each of the tissue fractions. However, the intensity of the signal was in the order of the luplin (+) fraction>the luplin (−) fraction>the stem>the leaf. This confirmed that the degree of mRNA derived from the farnesyl pyrophosphate synthase gene occupying in each tissue was the greatest in the luplin gland, next place in the stem and the bract, and the least in the leaf. In other words, it was confirmed that the farnesyl pyrophosphate synthase gene was expressed in the strongest manner in the luplin gland and thus the promoter of the farnesyl pyrophosphate synthase gene had the strongest promoter activity in the luplin gland.

INDUSTRIAL APPLICABILITY

As described above, it is possible to identify the farnesyl pyrophosphate synthase proteins and genes according to this invention. It will, therefore, reveal the genes involved in the biosynthesis of secondary metabolites in a hop as well as the nucleotide sequences of the promoter genes that function in the luplin gland of the hop in a tissue-specific manner. This will allow for the transformation of the hop by gene manipulations and the in vitro synthesis of the hop secondary metabolites.

What is claimed is:

1. An isolated nucleic acid encoding a protein comprising the amino acid sequence of SEQ ID NO: 1.

2. An isolated nucleic acid comprising the nucleotide sequence of SEQ ID NO: 3.

3. An isolated nucleic acid comprising the nucleotide sequence of SEQ ID NO: 2.

4. An isolated nucleic acid comprising nucleotides 1–1886 of SEQ ID NO: 2.

5. An isolated nucleic acid which hybridizes to nucleotides 1 to 1886 of SEQ ID NO: 2 or to a fully complementary nucleic acid thereof under stringent conditions, wherein said nucleic acid possesses promoter activity, and wherein the stringent conditions comprise hybridization in 6.0×SSC at 45° C. and washing in 0.1×SSC at 65° C.

* * * * *